United States Patent [19]

Takahashi et al.

[11] Patent Number: 5,308,990
[45] Date of Patent: May 3, 1994

[54] METHOD FOR MEASURING MICROPARTICLES, QUANTITATIVE MEASURING METHOD THEREFOR AND INSTRUMENT FOR MEASURING MICROPARTICLES

[75] Inventors: Satoshi Takahashi, Kokubunji; Daizo Tokinaga, Hachioji; Kazunori Okano, Shiki, all of Japan

[73] Assignee: Hitachi, Ltd., Tokyo, Japan

[21] Appl. No.: 882,954

[22] Filed: May 14, 1992

[30] Foreign Application Priority Data

May 15, 1991 [JP] Japan .................. 3-110336

[51] Int. Cl.$^5$ .................................. G01N 15/14
[52] U.S. Cl. ........................ 250/459.1; 250/458.1
[58] Field of Search ............ 250/459.1, 461.2, 461.1, 250/458.1

[56] References Cited

FOREIGN PATENT DOCUMENTS 56-151357 11/1981 Japan .
58-41336 3/1983 Japan .
64-35345 2/1989 Japan .

*Primary Examiner*—Paul M. Dzierzynski
*Assistant Examiner*—Richard Hanig
*Attorney, Agent, or Firm*—Antonelli, Terry, Stout & Kraus

[57] ABSTRACT

A microparticle measuring method according to the present invention, by which the number of fluorescent microparticles is counted and the fluorescent microparticles are analyzed, includes the steps of introducing fluorescent microparticles into a narrow flow path almost one after another; irradiating the fluorescent microparticles in the narrow flow path with excitation light; detecting a signal pulse produced by detection of a single photon of fluorescence generated by the irradiation with the excitation light; and recognizing existence of the fluorescent microparticle, starting from the number of signal pulses measured per predetermined standard period, and further includes the step of obtaining the number of signal pulses per standard period with a time interval shorter than the standard period. It further includes the step of counting successively the number of signal pulses generated in the predetermined standard period to recognize existence of the fluorescent microparticle, when the count value exceeds a predetermined threshold, and the kind of the fluorescent microparticles is estimated from the count value. Particularly by using microparticles having a diameter smaller than 0.1 $\mu$m as label material, reaction efficiency of the label material is increased, stability of the binding with the material to be measured is raised, and the material to be measured can be detected with a high precision and a high sensitivity.

8 Claims, 9 Drawing Sheets

METHOD FOR MEASURING MICROPARTICLES, QUANTITATIVE MEASURING METHOD THEREFOR AND INSTRUMENT FOR MEASURING MICROPARTICLES

BACKGROUND OF THE INVENTION

The present invention relates to a method for measuring microparticles and an instrument for measuring microparticles capable of detecting microparticles having a very low fluorescence intensity existing in liquid with a high precision to analyze them as well as to a quantitative measuring method and an instrument for realizing the same, useful in fields of immunological analysis and genetic diagnosis using microparticles.

(a) As a method for analyzing particles, etc., there is known an analyzing method using a flow cytometer. In the flow cytometer, liquid containing particles is led to a sheath flow cell so that particles flow separately one after another through an approximately central portion thereof, the particles flowing therethrough are irradiated with laser light, and scattered light or fluorescence (in the case where the particles are fluorescent) thus produced is detected by means of a photodetector such as a photomultiplier, etc. By this method the property of the particles can be analyzed by using pulse heights or integrated values of an output signal of the photodetector as a function of a time for the passage of a particle through the laser light. In order to increase the analysis precision by such a method, there are known a method, by which pulse width information is added to the pulse height, as described e.g. in JP-A-Sho-58-41336, and a method, by which the time of starting analysis of the pulse height or the integrated value is substantially advanced by delaying the signal pulses, as described in JP-A-SHo-65-35345.

(b) On the other hand, as an immunological measurement method using particles, there is known a method, by which antigen concentration is measured by making latex spheres, with the surface of which an antibody is bound, react with an antigen and measuring the agglutinated state of the latex spheres produced by the antigen-antibody reaction by the absorbance or the intensity of scattered light. Further, in order to analyze this agglutinated state with a high precision, there is known also a method, by which each agglutinated lump is led to a flow cytometer to be analyzed there. By this method it is possible to calculate the magnitude of each agglutinated lump, based on the intensity of scattered light to measure the antigen concentration with a high precision. This method is described e.g. in "Kensa to Gijutsu (Test and Techniques)" Vol. 16, No. 7 (1988), pp. 607-613.

(c) Further, as described e.g. in JP-A-SHo-56-151357, there is proposed a method by which particles having a diameter of about 0.5 μm are made to bind with an antigen to be measured by a reaction of a heterogenous system to measure the antigen concentration while counting the number of particles by means of a microscope.

SUMMARY OF THE INVENTION (a) By the flow cytometer described above, only the intensity of direct current of a photodetector is measured, because fluorescence intensity, produced when an individual particle passes through the region irradiated with laser light is measured by means of a photodetector such as a photomultiplier, an to obtain signal pulses from variations thereof with respect to time. For this reason, if the fluorescence intensity is sufficiently high with respect to a noise level, a signal pulse based on the passage of a particle can be recognized with a high precision. However, if the fluorescence intensity is decreased by factors such as the diameter of the particles is decreased, etc., since thermal noise or shot noise increases relatively, a S/N ratio of the fluorescence intensity is lowered. When the S/N ratio of the fluorescence intensity is lowered, recognition of the signal pulse based on the passage of the particle is worsened, measurement precision is lowered and thus analysis of the property of the particle becomes more difficult. This phenomenon is remarkable, particularly when the fluorescence intensity is in a single photon event state. In this state, since the time interval between a photon arriving at the photodetector and a next arriving photon is longer than the response time of the photodetector, the signal pulse height is no longer proportional to the fluorescence intensity and therefore by the by the methods, by which the signal pulse height, etc., are measured, it is not possible to measure precise fluorescence intensity. That is, when the fluorescence intensity is low, e.g. when the amount of fluorophore in the particles is small or when the intensity of the exciting light such as laser light, etc., is low, by the prior art methods it is difficult to measure it precisely.

(b) By the immunological measurement method by agglutination of particles, as described previously, a suspension containing agglutinated lumps having various magnitudes formed by the agglutination is measured by means of a flow cytometer. By this method the magnitude of each agglutinated lump can be measured and thus it is possible to increase the precision of calculating the antigen concentration. However, by this method, it is difficult to remove dust from the suspension or to eliminate influences of scattered light from the flow cell or the solvent itself. It is difficult also to eliminate completely influences of scattering matter, or flurorophores such as organic dyes existing in a sample. Further, since an antigen and a microparticle are not in a one-to-one correspondence, errors are apt to be produced in the calculated value of antigen concentration, particularly in an extremely low concentration region, by the prior art method, by which the number of agglutinated lumps is counted.

(c) For the method disclosed in JP-A-SHo-56-151357, by which a reaction in a heterogeneous system is utilized, the diameter of particles which can be used is not specifically set.

However, since a microscope is used for observing particles in a liquid, the size of the particles which can be used is determined by the resolving power, etc., of the microscope. As observing methods by means of a microscope, observation of transmitted light, scattered light and fluorescence can be cited. By observation of transmitted light or scattered light, it is difficult to distinguish the particles from dust, etc., existing in the solution. In order to decrease influences of dust, etc., it is preferable to observe the particles by the fluorescence method.

However, if the diameter of the particles is decreased, the fluorescence intensity of the particles is also decreased so that observation is difficult by usual methods. For this reason it is necessary that the used particles have a diameter greater than 0.1 μm. Precisely speaking, the limit of detection is determined by the kind of the fluorophore in the particles and the number of molecules thereof and in reality, it is useful to use particles having a diameter greater than 0.2 μm.

However, when the diameter of particles increases, another problem takes place. That is, when the diameter of the particles increases, since the diffusion velocity of the particles in the solution decreases, this can decrease the reaction velocity. Further, since the particles are too big with respect to antigen molecules, there exists also a possibility of reaction hindrance that for a plurality of antigen molecules, which can exist in regions smaller than the size of the particles, a number of particles corresponding to the number of the antigen molecules cannot be bound.

Furthermore, since the degree of dispersion of the microparticle suspension is small, the reaction is non-uniform and there is a possibility that the measurement precision of the antigen concentration is lowered. Still further, when the diameter of the particles increases, a force acting on each particle becomes great, and binding thereof with antigen molecules becomes relatively weak. Therefore the binding is apt to be broken and the measurement precision is lowered.

Since there exists the problem as described above for the particles having a great diameter, it is necessary to avoid them. That is, in order to increase the measurement precision for the immunological reaction and to shorten the reaction time, it is preferable to use microparticles having a smaller diameter.

However, when the diameter is decreased, the fluorescence intensity is also decreased.

By the prior art methods, in the published documents described above, etc., there is no explanation on the observation method for the case of such weak signals. By a usual method, when microparticles having a diameter smaller than about 0.1 μm are used, it is difficult to discern and count the particles.

An object of the present invention is to provide a microparticle measuring method and a measuring instrument having a sensitivity, capable of solving such problems of the prior art techniques and discerning precisely microparticles having a low fluorescence intensity.

Another object of the present invention is to provide a microparticle measuring method and a measuring instrument capable of measuring precisely variations in time in the fluorescence from fluorescent microparticles and measuring the total fluorescence intensity of individual fluorescent microparticles detected at random in time without count loss with a high precision so that the fluorescent microparticles can be analyzed with a high precision.

Still another object of the present invention is to provide a microparticle measuring method, by which direct counting of label material is possible, reaction efficiency of the label material is increased and the stability of the binding with the material to be measured is increased so that the amount of the material to be measured can be measured with a high precision and a high sensitivity.

Still another object of the present invention is to provide a measuring method suitable for using in particular microparticles having a diameter smaller than 0.1 μm as label material.

The microparticle measuring method according to the present invention is characterized in that (A) it comprises a processing of leading almost one microparticle into a position irradiated with light or sweeping successively a light beam adjusted to be able to irradiate a region in which almost one microparticle can exist; a processing of taking out a signal pulse, based on detection of a single photon of fluorescence produced by irradiation with the light; a processing of counting of the number of pulses for every predetermined standard period (the standard period used in the present specification is related to a working time of a counter working periodically and the standard period is either equal to the working time itself of the counter or it means one Nth (N being an integer) of the working time of the counter) with a time interval shorter than the standard period; and a processing of recognizing existence of the microparticle in real time, on the basis of the number of signal pulses measured for every standard period.

Further, it is characterized in that (B) a count value of signal pulses measured for every predetermined standard period is obtained by a processing of counting the signal pulses successively with a predetermined period shorter than the standard period and a processing of storing count values of at least consecutive two periods and accumulating the stored count values of the at least two periods for every period, and the time for obtaining the count value by accumulation is made equal to the standard period described above. It is characterized further in that it includes a processing of recognizing the existence of the microparticle on the basis of the accumulated value.

Still further it is characterized also in that (C) the number of signal pulses produced in the predetermined standard period is counted successively and the existence of the microparticle is judged in real time, when the count value exceeds a predetermined threshold, and the kind of the microparticle is judged in real time on the basis of the count value.

It is characterized also in that (D) the count value of the signal pulses measured for every predetermined standard period is obtained by using N counters, N being not smaller than 2 ($N = \geq 2$), which are driven with a period T longer than the standard period, the counting working time of each of the counters being set at the standard period, the phases of the different counters being different from each other, and by taking out the count value of a suitable counter for every working interval of T/N, T/N representing a shift in the working time between an n-th ($N \geq n \geq = 2$) counter and an (n−1)-th counter, i.e. the working interval.

Further it is characterized also in that (E) the standard period is set so as to be either approximately equal to a period of time, during which the microparticle is irradiated with light, or shorter than a period of time, which is about two times as long as the period of time, during which the microparticle is irradiated with light.

Furthermore, a microparticle measuring instrument according to the present invention is characterized in that it comprises (F) (a) exciting light emitting means for producing fluorescence from microparticles; (b) fluorescence focusing means for focusing fluorescence from microparticles; (c) detecting means for taking out an electric pulse (i.e. signal pulse), based on the detection of a single photon of the fluorescence; (d) counter means for counting the number of electric pulses; (e) counter control means for controlling working times and periods of counters as well as intervals of the counting operation between different counters; (f) count value selecting means for taking out successively the count value of each counter after a counting operation in every single counting working period of each of the counters has been terminated and (g) peak detection means for detecting a peak of the count value.

Further, it is characterized also in that (G) the counter control means sets the counting working time so as to be equal to the standard period and controls the interval of operation between the different counters so as to be shorter than the counting working time. Still further, it is characterized also in that (H) a comparing circuit for comparing the count value obtained by the count value selecting means with a predetermined threshold is disposed between the count value selecting means and the peak detecting means.

(I) A microparticle counting instrument, which counts microparticles in a liquid, based on optical variations in light emitted by the microparticles to analyze the microparticles, is characterized in that it comprises at least (a) light detecting means for taking out an electric pulse, based on detection of a single photon of light emitted by a microparticle; (b) at least a counter for counting the number of electric pulses successively with a predetermined repetition period; and (c) an accumulating circuit for storing count values for more than 2 consecutive periods and accumulating the count values for more than 2 periods, which are stored separately for every period.

Further, it is characterized also in that (J) the predetermined repetition period, with which the counting operation of the counters described in (I) is effected, is shorter than the time, during which the microparticles are irradiated with light, and the counting time necessary for obtaining the count value obtained as the result of the accumulation is either almost equal to the fluorescence production time from the microparticles or 1 to 2 times as long as the fluorescence production time.

Still further, the measuring means by means of microparticles according to the present invention is characterized in that (K) it comprises a processing, by which, using a solid phase, on which a material bound specifically with the material to be measured in the sample solution is immobilized or a solid phase, with which the material to be measured can be bound, and fluorescent microparticles, on which the material bound specifically with the material to be measured is immobilized the microparticles are bound with the solid phase by bringing the solid phase, the material to be measured and the microparticles into contact with each other, and a processing, by which the microparticles thus bound are measured by the microparticle measuring method.

Furthermore, it is characterized also in that (L) microparticles having a diameter smaller than 0.1 $\mu$m are used for the microparticles.

According to the present invention, a photomultiplier, etc., are used for the photodetector; incident photons are converted into electric pulses by the photoelectron counting method; the number of pulses is counted; and the fluorescence intensity is measured. This photoelectron counting method makes elimination of a noise component easier and a measurement at a high S/N ratio possible by pulse height discrimination using the fact that the pulse height based on the photon detection and the pulse height based on noises such as thermal noise, etc., are different from each other.

At first, (a) the particles are irradiated with excitation light by an excitation light emitting unit to produce fluorescence. Laser light, e.g. light of an argon ion laser, a helium-neon laser, a helium-cadmium laser, a YAG laser, a semiconductor laser, etc., is suitable for the excitation light. Further, light of a xenon lamp or a mercury lamp can be used therefor. (b) Fluorescence thus produced is focused by a fluorescence focusing unit. (c) A light detection unit detects the fluorescence and outputs electric pulses according to the detection of a single photon. (d) The counter unit counts the number of electric pulses by means of a plurality of counters. (e) The counter control unit controls the working time and the period of the different counters as well as the operation interval between the different counters to drive them. (f) The count value of the different counters are taken out successively for every operation interval by the counter value selecting unit. (g) The count value obtained by the count value selecting unit is compared with a threshold level by the comparing circuit unit, which makes the count value pass through, when it exceeds the threshold level. (h) The peak value of the count value exceeding the threshold level is detected by the peak detection unit. This peak value is analyzed by the data processing unit.

In order to measure bound fluorescent microparticles in the reaction sampling tube, the focal point of a microscope is adjusted to a position, where a fluorescent microparticle exists; microparticles are irradiated with laser light almost one after another while sweeping a laser light beam in the X- directions or moving a stage in the X-Y directions; variations in fluorescence thus produced are measured by the microparticle measuring method described above; and the number of microparticles is counted in real time. Further, a microparticle suspension is prepared by stripping off physically or chemically fluorescent microparticles bound by the reaction sampling tube therefrom. This microparticle suspension is led to a light measuring cell such as a sheath flow cell, etc., and the position irradiated with excitation light is so adjusted that the microparticles pass therethrough almost one after another. In this way, fluorescence is measured by the microparticle measuring method described previously and the number of microparticles is counted.

The fluorescent microparticles used for the present invention can be obtained by having a fluorophere contained within the microparticles or by binding the fluorophone with the surface of the microparticles. For the material of the microparticles e.g. polystyrene, polymethylmethacrylate, styrene-butadiene copolymer, etc., can be used. Further, a microparticle-shaped material having a structure, in which a framework is made of polyamideamine, can be used. Further, it is necessary for the microparticles used for the reaction to be bound with a material capable of being bound specifically with the material to be measured in the sample. As a combination of the material to be measured in the sample and the material bound specifically therewith, an antigen (or an antibody) and an antibody (or an antigen) is a representative combination. Other examples are a combination of a hormone and a receptor, a combination of specified DNA and probe DNA produced by a hybridization reaction, etc. Known methods such as physical adsorption, chemical binding, etc., can be used for binding an antibody (or an antigen) with the surface of a microparticle.

As explained above, according to the present invention, since the fluorescence intensity from fluorescent microparticles is measured through the number of photons thereof, noise can be reduced. Further, since discrimination of the fluorescent microparticles is carried out by measuring the number of photons of the detected fluorescence, it is possible to discriminate microparticles having a low fluorescence intensity with a high precision. Still further, since the number of photons detected for every standard period can be measured with a time interval shorter than the standard period, time variations in the fluorescence from the fluorescent microparticles can be measured with a high precision. As the result it is possible to measure fluorescent microparticles detected at random in time without losing counting timing and to measure precisely the total number of photons emitted by the fluorescent microparticles. Further, according to the present invention, since it is possible to discriminate microparticles having diameters smaller than 0.1 μm, fluorescent microparticles having diameters small than 0.1 μm can be used as label material. As a result, direct count of the label material is made possible and reaction efficiency of the label material is increased. Thus, the stability of the binding with the material to be measured is increased and it is possible to measure, the quantity of the material to be measured with a high precision and a high sensitivity.

DESCRIPTION OF THE PREFERRED EMBODIMENTS

Figure 1:
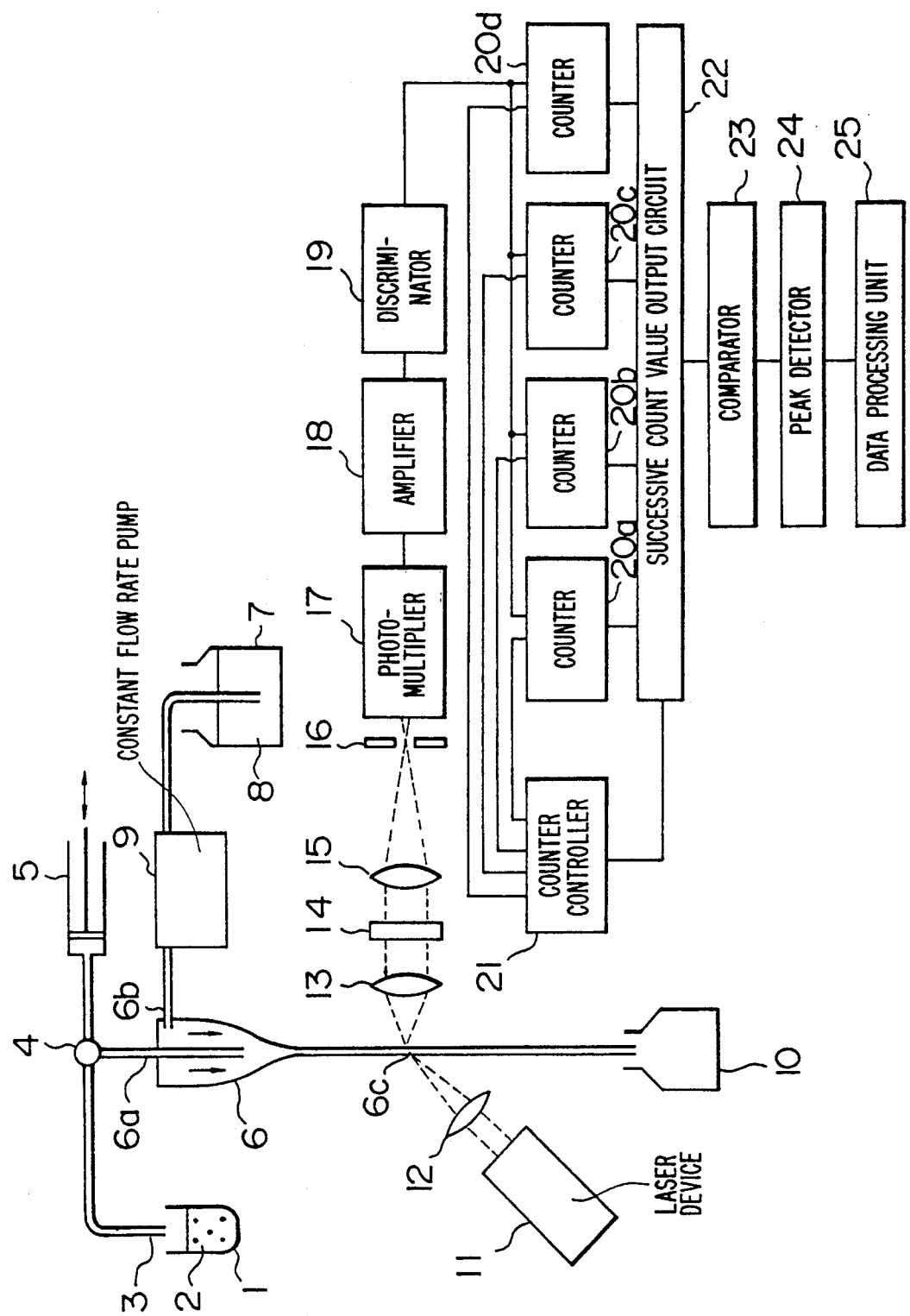
FIG. 1 is a block diagram of an instrument for measuring fluorescent microparticles indicating an embodiment of the present invention.

Hereinbelow some preferred embodiments of the present invention will be explained in detail, referring to the drawings.

FIG. 1 is a block diagram indicating the construction of an instrument for measuring fluorescent microparticles, which is the first embodiment of the present invention.

The measuring instrument indicated in FIG. 1 is one, in which a fluorescent microparticle suspension is made to flow to be measured successively. This measuring instrument is composed of a sample introducing unit (3–6), an excitation light projecting unit (11, 12), a fluorescence collecting unit (13–16), a light detecting unit (17–19), a counter unit (20a–20d), a counter control unit (21), a count value selecting unit (22), a comparing circuit unit (23), a peak detecting unit (24) and a data processing unit (25). The construction indicated by the reference numerals 17 to 25 is the part newly added according to the present invention, while the construction indicated by the reference numerals 1 to 16 is the part known heretofore.

That is, the sample introducing unit consists of a nozzle 3 for sucking microparticle suspension 2 contained in a sampling tube 1, an electromagnetic valve 4 for switching over the flow path, a syringe pipetter 5 sucking and ejecting the sample, a sheath flow cell 6 for introducing the microparticle suspension 2 and a sheath solution 8, etc. The excitation light projecting unit is composed of a laser device 11 and a focusing lens 12. The fluorescence collecting unit is composed of focusing lenses 13 and 15, a spectral filter 14 and a slit 16. The light detecting unit is composed of a photomultiplier 17, an amplifier 18 and a discriminator 19. Further, the counting portion is composed of a plurality of counters 20a–20d. There are disposed a counter controller 21 for the counter control unit, a successive count value output circuit 22 for the count value selecting unit, a comparator 23 for the comparing circuit unit, and a peak detector 24 for the peak detecting unit.

Now the operation of the measuring instrument indicated in FIG. 1 will be explained. The sample suspension to be measured (microparticle suspension 2) and the sheath solution 8 are led to the sheath flow cell 6 so that the sample suspension 2 forms a fine stream enclosed by the sheath solution 8 in order to effect fluorescence measurement. For this purpose, microparticle suspension 2 contained in the sampling tube 1 is sucked by means of the syringe pipetter 5 through the nozzle 3 and the electromagnetic valve 4. Next the electromagnetic valve 4 is switched over so that the sucked microparticle suspension 2 is ejected with a constant flow rate through a sample introducing tube 6a of the sheath flow cell 6. At the same time, the microparticle suspension 2 narrowed down is made to flow through a light measuring portion 6c of the sheath flow cell by introducing the sheath solution 8 contained in a bottle of sheath solution 7 through the sheath solution introducing tube 6b of the sheath flow cell 6 by means of a constant flow rate pump 9 and is discarded finally in a waste bottle 10.

Next the fluorescence measurement will be explained. In order to excite fluorescent microparticles, laser light emitted by the laser device 11 is focused by the lens 12 to be projected on the microparticle suspension 2 flowing through the light measuring portion 6c in the sheath flow cell 6. An Ar ion laser or a semiconductor laser is used for the laser device 11. Fluorescence emitted by the fluorescent microparticles is collected by the lens 13 and scattered light is removed as far as possible by means of the spectral filter 14 such as a bandpass interference filter, etc. Transmitted fluorescence is collected again by the lens 15 and focussed on the slit 16. Only an image from a fluorescent microparticle passes therethrough and is detected by means of the photomultiplier 17 serving as a photodetector. An output of the photomultiplier 17 is amplified by the amplifier 18. Thus, photons injected into the photomultiplier 17 are converted into a pulse signal (electric pulse), which is outputted through the discriminator 19, by the photoelectron counting method.

Next, pulse signals based on the detection of the photons are counted by the counters 20a-20d. The operation of the counters is controlled by the counter controller 21. The working period of each of the counters is a constant time and they are driven at phases, which are shifted by a time interval, which is equal to ¼ of the working period, from each other. The working period is set so as to be almost equal to the time necessary for a fluorescent microparticle to pass through the excitation light beam. The count value of each of the counters is inputted to the successive count value output circuit 22 for every period and that value is held, until a new count value is inputted thereto. As the result a stepwise pulse waveform indicating the count value for one period for every ¼ period is obtained in the successive count value output circuit 22. A result thus obtained is outputted to the comparator 23. The comparator 23 compares the count value with a predetermined threshold and sends it to the peak detector 24, when the count value exceeds the threshold. This threshold is disposed for the purpose of reducing influences of noise such as scattered light, which doesn't depend on the fluorescence from the fluorescent microparticles, and it is set depending on the state of the optical system in the instrument, etc. The peak detector 24 detects the peak value in real time, from variations in time in the count values exceeding the threshold. In order to analyze this peak value, the data processing unit 25 effects various processings of accumulating the frequency of different peak values, calculating the total number of peak pulses having the peak value in each of specified regions, i.e. the number of microparticles, etc. The detection of the peak is effected almost at the same time as the passage of the microparticle and treated in real time. For this reason, the time for measuring the sample is not limited and thus a long term measurement is made possible.

Figure 2:
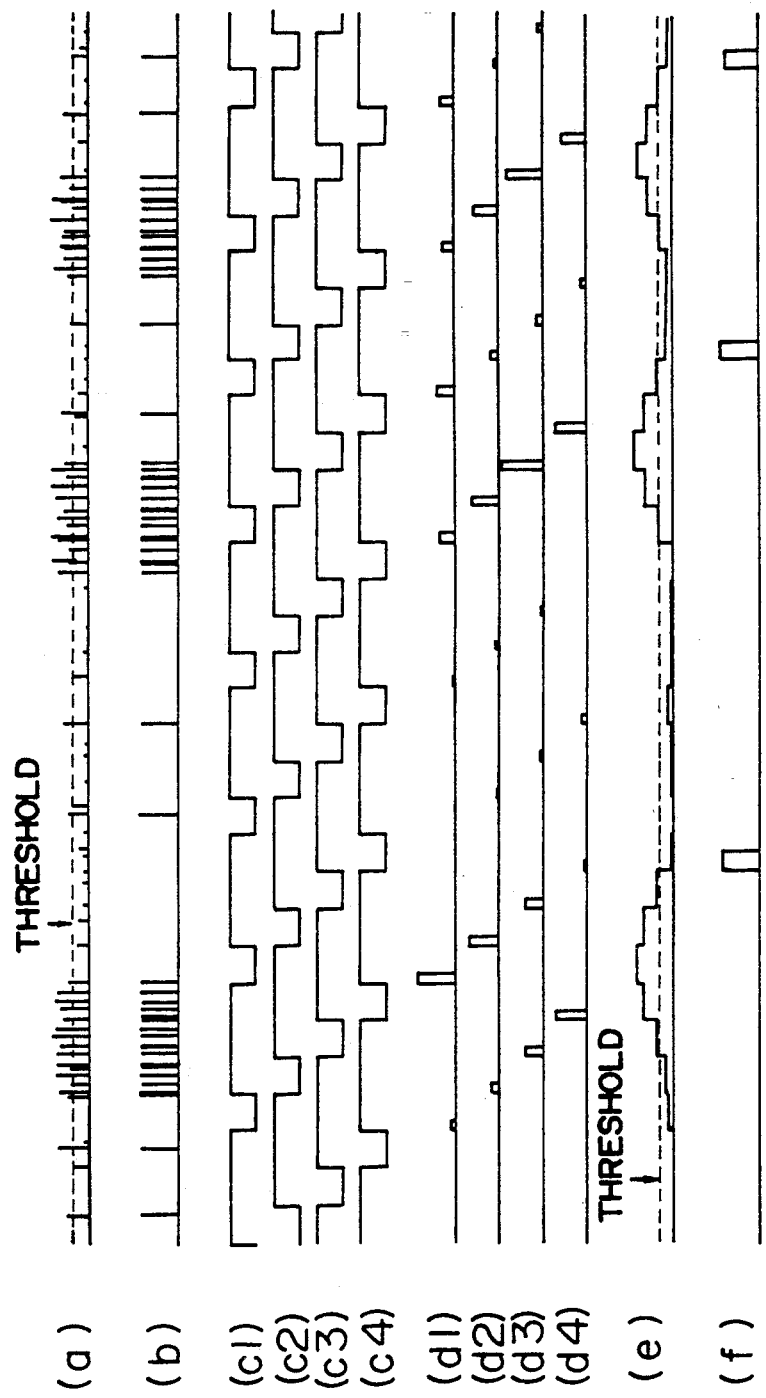
FIG. 2 is a time chart representing a flow of signal processing in the instrument indicated in FIG. 1.

FIG. 2 is a timing chart indicating a flow of signal processing in the instrument in FIG. 1.

(a) in FIG. 2 represents variations in time in the output of the photomultiplier 17. This output includes relatively great pulses based on the detection of a single photon and relatively small pulses based on dark current of the photomultiplier 17 itself. The amplifier 18 and the discriminator 19 separate them, using the threshold (indicated by a broken line) as the boundary therebetween. As indicated by (b) in FIG. 2, only the pulses based on the detection of a single photon are taken out. (c1) to (c4) indicate variations in time in the state of the gates of 4 counters 20a to 20b controlled by the counter controller 21. Here, the counters 20a to 20d are driven so as to effect counting operation at the high level and set so that the phases thereof are shifted by ¼ period from each other. Variations in time in the outputs of the counters 20a to 20d corresponding to (c1) to (c4) are as indicated in (d1) to (d4), respectively. After the counting operation, the counters output pulses indicating the respective count values and repeat this operation. These outputs are sent to the successive count value output circuit 22. The successive count value output circuit 22 outputs a signal varying stepwise for every ¼ period, as indicated in (e). The ordinate of (e) represents the count value. In order to eliminate influences of the count corresponding to dark pulses, a suitable threshold is selected and the peak value of the count value exceeding this threshold is taken out by the peak detector 24. (f) represents the output of the peak detector 24. Further, the peak value of (f) is outputted almost at the same time as the passage of the microparticle. The peak value indicates the fluorescence intensity of the microparticle and further the fluorescence intensity represents the magnitude of the microparticle. That is, by this signal processing, it is possible to effect the detection in real time, including information on the magnitude of the microparticle. The frequency of this pulse height is analyzed by the data processing unit 25 constituted by a pulse height analyzer and the number of microparticles is calculated, starting from the number of production of pulses having the pulse height in a specified region.

Figure 3:
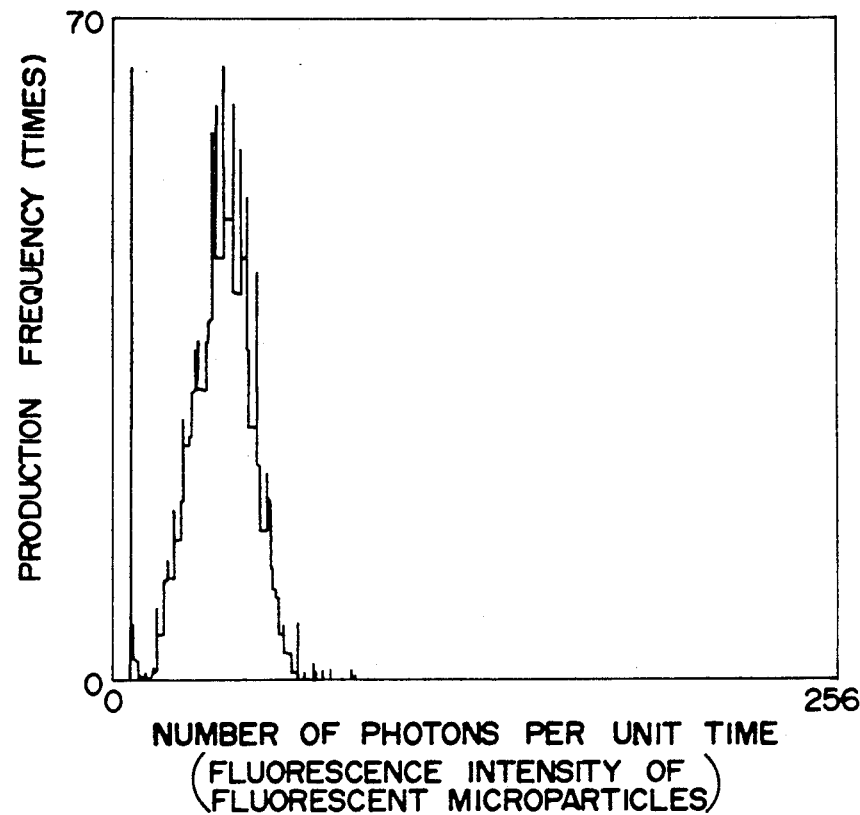
FIG. 3 is a histogram indicating the relation between the number of photons detected for every standard period obtained by means of the instrument indicated in FIG. 1 and the production frequency thereof.
Figure 4:
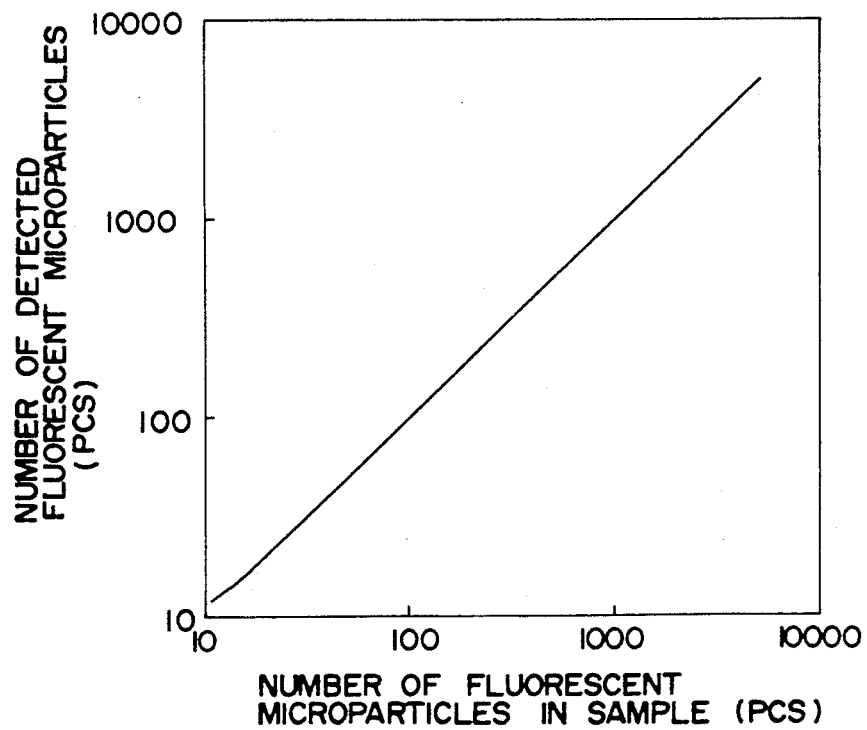
FIG. 4 is a graph representing the relation between the total number of fluorescent microparticles contained in a sample and the total number of detected fluorescent microparticles obtained by means of the instrument indicated in FIG. 1.

FIG. 3 shows an example of the relation between the number of photons detected for every standard period (fluorescence intensity of fluorescent microparticles) and the production frequency thereof, i.e. a histogram, obtained by means of the instrument indicated in FIG. 1. FIG. 4 is a graph indicating the relation between the total number of fluorescent microparticles contained in the sample and the total number of detected fluorescent microparticles obtained by means of the instrument indicated in FIG. 1.

Hereinbelow a concrete example of the instrument in FIG. 1 will be described. An argon ion laser (wavelength of 488 nm, output of 10 mW) is used and light emitted thereby is suitably attenuated. This is focused to a beam having a diameter of about 20 $\mu$m and the light measuring portion 6c in the sheath flow cell 6 is irradiated therewith. Polystyrene microparticles containing fluorescein (diameter 0.09 $\mu$m) are used for the fluorescent microparticles. The microparticle suspension 2 is led to the sheath flow cell 6. The microparticle suspension 2 is finely narrowed so as to have a diameter of about 10 $\mu$m and is made pass through the light measuring portion 6c. The flow speed is adjusted to about 0.5 m/s. Produced fluorescence is collected by the objective lens 13 having a magnification factor of 40 and transformed into a parallel light beam. Scattered light is removed by an interference filter 14 transmitting light of 510 to 550 nm. Further, an image of flowing fluorescent microparticles is focused on the slit 16 having a rectangular aperture having a width of 500 $\mu$m and a length of 1 mm. Fluorescence passing through the slit is detected by the photomultiplier 17 and subjected to the signal processing described above. The counting working time is 60 $\mu$s and the working period of the counters 20a to 20d is 65 $\mu$s. The result obtained at this time is as indicated in FIG. 3. The abscissa in FIG. 3 represents the peak value obtained by the peak detector 24, which means the number of photons of the fluorescence detected for every standard period (counting working time 60 $\mu$s) and is proportional to the fluorescence intensity. On the other hand, the ordinate in FIG. 3 represents the production frequency of the relevant value. The protrusion for small numbers of photons on the abscissa represents a part of the tail of the protrusion due to noise. That is, at places close to 0 in the number of photons, the ordinate represents the number of noises due to scattered light, etc., corresponding to a part of the base of the protrusion remaining after having cut-off the last at the threshold. Further, different points constituting the protrusion at great numbers of photons represent different fluorescent microparticles and the value obtained by integrating this protrusion indicates the total number of detected fluorescent microparticles.

When the measurement is effected, varying the concentration of the microparticle in the microparticle suspension 2, which is the sample, the relation between the total number of fluorescent microparticles in the sample and the total number of the detected fluorescent microparticles can be represented by a characteristic curve as indicated in FIG. 4.

As clearly seen therefrom, a linear relationship therebetween can be held from a low concentration to a high concentration and a high measurement sensitivity is obtained. Further, the reproducibility is also high.

In the present embodiment, since the fluorescence measurement is effected by the photoelectron counting method, it is possible to measure the fluorescence intensity with a high sensitivity in principle. Consequently, it is possible to count fluorescent microparticles having a low fluorescence intensity, i.e. microparticles having a small size, microparticles, for which the amount of the fluorescent material existing in the interior or on the surface of the microparticles is small, microparticles containing a fluorescent material having a small fluorescence yield, etc., with a high precision. Further, since the counting can be effected without increasing the excitation light intensity and a semiconductor laser having a low light output can be used therefor, if a suitable fluorophore is chosen, down sizing of the instrument can be realized. Further, in principle, both in the case where the number of microparticles is measured by measuring the whole quantity of the microparticle suspension and in the case where the number of microparticles calculated while measuring a part of the microparticle suspension, since the fluorescent microparticles can be counted one after another, it is possible to measure the fluorescent microparticles with a high sensitivity and a high precision.

Furthermore, by controlling the counters so that the counting working time is kept constant for a plurality of counters and the working interval between different counters is shorter than the working time by shifting the working phases of the different counters, as in the present embodiment, it is possible to take out the count value for a working time of the counters with a finer time interval and to count it with a high precision. Further, for this reason, it is possible to effect the measurement without missing fluorescence photons from the microparticles detected at random in time and to measure the fluorescence intensity of the microparticles passing through the light measuring portion at an arbitrary timing with a high precision. Although FIG. 1 indicates a case where there are 4 counters, the instrument may be constructed with n counters, n being greater than 2. In this case, this can be realized by driving the counters with working phases shifted by 1/n period from each other and by reading in the count values thereof one after another. Further, the comparator 23 is useful for decreasing the frequency bandwidth of the succeeding circuit, and it is possible also to make use of the comparator unnecessary by making the bandwith of the peak detector 24, the data processing unit 25, etc., sufficiently wide. Furthermore, although, in FIG. 1, the pulse height representing the number of photons for every standard period is analyzed by the pulse height analyzer, in the case where the distribution is known previously, it is possible also to count pulses by means of a counter counting only peak values in a predetermined region.

In the present embodiment, the peak value ((f) in FIG. 2) is detected and outputted almost at the same time as the passage of the microparticle. That is, since the detection of microparticles can be effected in real time, the measuring time is not limited. In the case where all the outputs of the counters are subjected to data processing after having been stored in a memory, the measuring time can be limited by the capacity of the memory and the period of the counters. For example, supposing that the capacity of the memory is 1M bytes, the period of the counters is (65/4) µs, and 1 data set consists of 2 bytes, the total measuring time is about 8 seconds and thus it is impossible to have a satisfactory measuring time. In the case of the present embodiment, since the microparticles can be detected in real time and only information on the magnitude of the fluorescence intensity is stored in the memory in the pulse height analyzer, the memory can be used efficiently and deal with a long term measurement. As described above, the time for measuring the sample is substantially not limited. Further, in the case where only the number of detected microparticles is counted, the construction of the instrument can be simplified.

Figure 5:
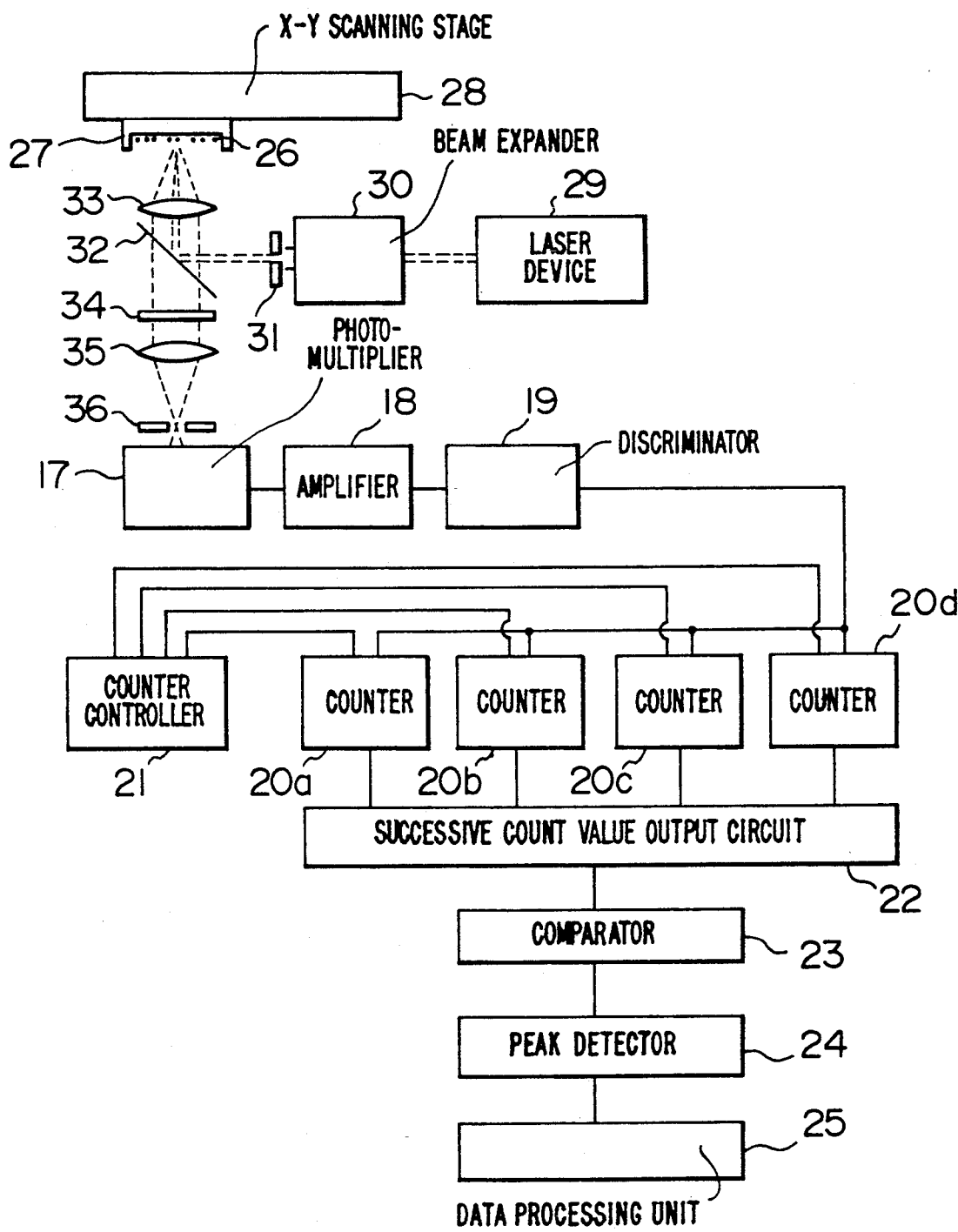
FIG. 5 is a block diagram of an instrument for measuring fluorescent microparticles indicating a second embodiment of the present invention.

FIG. 5 is a block diagram indicating the construction of a microparticle measuring instrument, which is a second embodiment of the present invention.

While FIG. 1 indicates a method for counting the number of microparticles in liquid containing them, e.g. in a microparticle suspension 2, FIG. 5 indicates a method for measuring fluorescent microparticles stuck to a substrate. Here, the suspension 2 containing fluorescent microparticles having carboxyl groups on the surface is put on a glass substrate 27 such as a slide glass, etc., to stick the fluorescent microparticles to the surface of the glass, in order to count the number of fluorescent microparticles.

In FIG. 5, the construction from the photomultiplier 17 to the data processing unit 25 is identical to that indicated in FIG. 1. The glass substrate 27, to which fluorescent microparticles 26 are stuck, is held on an X-Y scanning stage 28 to be scanned in the X-Y directions. Irradiation with excitation light and collection of fluorescence are identical to those used for a downward projection fluorescence microscope. An excitation laser light beam emitted by a laser device 29 is enlarged by means a beam expander 30. A transmitted laser light beam is d by a slit 31 having a square aperture and reflected by a dichroic mirror 32. Then it is narrowed by an objective lens 33 and projected downward to a fluorescent microparticle 26 on the glass substrate 27. Fluorescence emitted by the fluorescent microparticle is collected by the objective lens 33. Scattered light is removed as far as possible by means of the dichroic mirror 32 and a spectral filter 34 such as a bandpass interference filter, etc. Next, transmitted fluorescence is collected again by a lens 35 so as to be focused on a slit 36. Only an image coming from the fluorescent microparticle passes therethrough and is detected by the photomultiplier 17 acting as the photodetector. The output of the photomultiplier 17 is amplified by the amplifier 18 by the photoelectron counting method in the same way as for the case indicated in FIG. 1. Thereafter, it passes through the discriminator 19 and in this way photons injected into the photomultiplier 17 are transformed into a pulse signal to be outputted. The pulse signal based on this photon detection is subjected to signal processing in the same way as for the case indicated in FIG. 1. The number of photons detected for every standard period is monitored in real time and analyzed.

In FIG. 5, an argon ion laser (wavelength of 488 nm, output of 5 mW) is used for the laser device 29 and light emitted thereby is suitably attenuated. The fluorescent microparticle is irradiated with a spot of 1 μm square. The X-Y scanning stage 28 is moved with a speed of 5 mm/s in the X-Y directions one after another. The working time of the counter at this time is 200 μs. The result obtained at this time is represented by a histogram having a distribution similar to that indicated in FIG. 3.

In the embodiment indicated in FIG. 5, it is possible to measure the fluorescent microparticles bound with a flat part of the glass substrate, etc., in the state as it is. Further, since the number of photons of fluorescence in the standard period is measured by the photoelectron counting method, it is possible to count fluorescent microparticles having a low fluorescence intensity with a high precision. Further, although FIG. 5 indicates a case where the glass substrate is moved in the X-Y directions by means of the X-Y scanning stage to analyze the number of microparticles on a plane, it is possible to analyze it similarly by sweeping the laser light beam serving as excitation light.

Now a third embodiment of the present invention will be explained. That is, the third embodiment shows a measuring instrument using a semiconductor laser device.

In FIG. 1, a semiconductor laser having a wavelength of 670 nm may be used for the laser device 11. In this case, since fluorescein, etc., cannot be used as the fluorophore, a substance having absorption around a wavelength of 670 nm is used. For example, aluminium phtalocyane complex, etc., can be used. Fluorescence is measured by using microparticles containing this aluminium phtalocyane complex, etc., or microparticles, at the surface of which it is are bound, and the semiconductor laser light as excitation light. The diameter of the fluorescent microparticles, for which the fluorophore is aluminium phtalocyane complex, is 0.1 μm. A bandpass interference filter transmitting light of a wavelength region from 695 nm to 750 nm is used for the spectral filter for detecting the fluorescence. A photomultiplier sensitive to longer wavelengths is used for the photodetector, whose photoelectric surface is cooled. The other processings, e.g. introduction of the fluorescent microparticle suspension into the flow cell, signal processing, etc. may be effected in the same way as in the first embodiment indicated in FIG. 1. In this way a result having a distribution almost identical to that indicated in FIG. 3 can be obtained.

In the third embodiment, since the fluorescence measurement is effected by the photoelectron counting method, the fluorescence intensity can be counted with a high sensitivity in principle. Consequently it is possible to count fluorescent microparticles having a low fluorescence intensity with a high precision. As a result, signals from the fluorescent microparticles can be obtained efficiently even with a semiconductor laser instrument having a low light output, and thus the fluorescence can be measured with a high sensitivity and a high precision. Further, since a semiconductor laser can be used for the light source for exciting the fluorescent material, down sizing of the whole instrument can be expected. Furthermore, since the excitation light has longer wavelengths, it is easier to suppress scattered light and it is possible to fabricate an instrument at a low cost.

Next a fourth embodiment of the present invention will be explained. The fourth embodiment represents a case where two kinds of fluorescent microparticles are counted while being discriminated separately.

Figure 6:
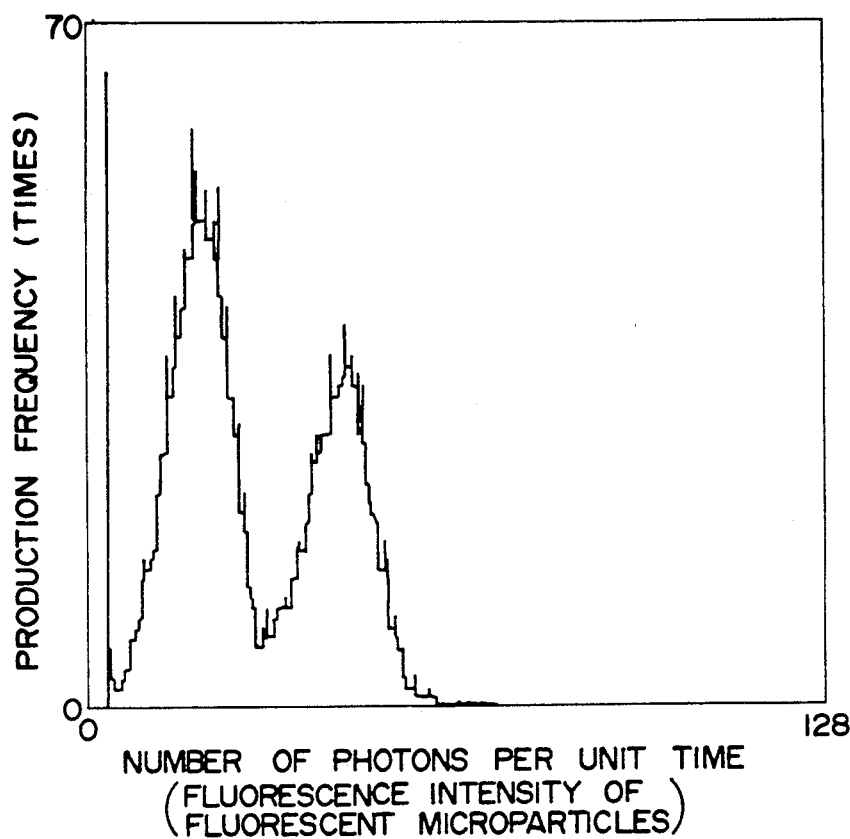
FIG. 6 is a histogram indicating the relation between the number of photons detected for every standard period and the production frequency thereof, in the case where 2 kinds of fluorescent microparticles are measured simultaneously.

A mixture of polystyrene microparticles having a diameter of 0.09 μm containing fluorescein and polystyrene microparticles having a diameter of 0.06 μm containing fluorescein is used for the fluorescent microparticles. When this microparticle suspension is analyzed by means of the measuring instrument indicated in FIG. 1, a result as indicated in FIG. 6 is obtained. That is, a distribution having two peaks is obtained, which means that the fluorescent microparticles can be clearly divided into 2 groups, depending on the number of photons. Further, in order to eliminate influences of simultaneous passage of fluorescent microparticles, a fluorescent microparticle suspension having a satisfactorily low concentration is used. In FIG. 6, the abscissa represents the peak value of the number of fluorescence photons detected for every standard period, obtained by the peak detector, which is proportional to the fluorescence intensity. On the other hand, the ordinate represents the production frequency for these values. The peak corresponding to the greater number of photons on the abscissa represents a signal coming from the microparticles having a diameter of 0.9 μmm, while the peak corresponding to the smaller number of photons on the abscissa represents a signal coming from the microparticles having a diameter of 0.6 μm. It is possible to discern the kind of microparticles by using the valley portion therebetween. As described above, in the present embodiment, it is possible to discern 2 kinds of fluorescent microparticles individually, starting from the number of photons of fluorescence detected per standard period and to count them in real time.

In the present embodiment it is possible to discern fluorescent microparticles having different diameters individually and to identify and count a plurality of kinds of fluorescent microparticles. Further, the measurement can be effected both in the case where a same kind of fluorophore is used, as in the present embodiment, and in the case where fluorescent microparticles contain different kinds of fluorophores. In the case where one kind of excitation light is sufficient, a fluorescence detecting system may be disposed for each kind of fluorescent microparticles to analyze signals of each system. On the other hand, in the case where it is necessary to change the excitation light for different kinds of fluorescent microparticles, the analysis can be effected by disposing an excitation light optical system and a fluorescence detecting system for each kind of fluorescent microparticles.

Next, as a fifth embodiment of the present invention, an application of the microparticle measuring method to an immunological measurement will be explained.

A method and a measuring instrument for measuring quantitatively the antigen concentration by binding fluorescent microparticles with a reaction tube by the heterogeneous sandwich immunoassay method and by counting these fluorescent microparticles by means of the microparticle measuring instrument, will be described, taking human α-fetoprotein (human AFP) as an example.

At first, a solid phase for reaction is prepared, by using wells of a microtiter plate for the reaction tube and by immobilizing antibody in each of the wells. Further microparticles, on which the antibody is immobilized, are prepared for label microparticles. Thereafter, a sample, etc., are made to react therewith and the microparticles are measured.

PREPARATION OF THE SOLID PHASE FOR REACTION

The solid phase for reaction is prepared by immobilizing anti-human AFP antibody in a well of microliter plate. At first, 100 μl of a glutaraldehyde solution of 0.1% is injected into the well of microtiter plate made of polystyrene, having amino residues on the surface thereof. After having made them react with each other during one night at room temperature, the solution is removed and the rest is rinsed. Next 100 μl of an anti-human AFP antibody solution (concentration 1 μg/ml) is injected into the well. After having agitated them intermittently in 2 hours at the room temperature, they are made to react with each other for one night at 4° C. The reaction tube is prepared by rinsing them finally with a phosphate buffer solution containing 0.5% bovine serum albumin (BSA) (0.5% BSA-PBS).

PREPARATION OF LABEL MICROPARTICLES

Fluorescent microparticles made of polystyrene having carboxyl groups on the surface and containing fluorescent substance in the interior are used. Label microparticles are prepared by immobilizing antihuman AFP antibody on the surface of the fluorescent microparticles having a diameter of 0.09 μm and a maximum fluorescence wavelength at about 540 nm. Concretely speaking, anti-human AFP antibody (Fab', by treating anti-human AFP antibody ((Fab')$_2$) with 2-mercaptoethanol. Apart therefrom, the microparticles are treated with 1-ethyl-3-(3-dimethylaminopropyl)carbodiimide-hydrochloride, 1,8-diamino-3,6-dioxaoctane, and N-(γ-maleimidobutyryloxy)succinimide. The fluorescent microparticles, on the surface of which anti-human AFP antibody (Fab') is immobilized, i.e. the label microparticles, are obtained by making these fluorescent microparticles react with the anti-human AFP antibody (Fab') prepared previously. These label microparticles suspended in a phosphate buffer solution containing 1% BSA are used. The concentration of the label microparticles in the suspension is adjusted to be 0.1%. However the concentration is not restricted thereto, but determined depending on an object to be measured, a reaction time, the kind of microparticles, etc.

PROCEDURE OF REACTION

100 μl of the sample solution containing human AFP, which is a material to be measured, is injected into a reaction tube (well), on which anti-human AFP antibody is immobilized. They are made to react with each other for 2 hours at room temperature so as to bind the human AFP with the well through the anti-human AFP antibody. Thereafter the solution in the well is removed and the rest is rinsed with 0.5% BSA-PBS.

Next 100 μl of a label microparticle suspension adjusted so that the concentration of the microparticles is 0.1% is injected into the well. They are made to react with each other for 2 hours at the room temperature and label microparticles are bound with the human AFP caught by the well. Thereafter the solution in the well is removed and the rest is gently rinsed with 0.5% BSA-PBS to remove excess label microparticles.

PROCEDURE OF MICROPARTICLE MEASUREMENT

By the operation described above it is possible to bind label microparticles proportional to the amount of human AFP, which is the material to be measured, to the well. The number of these label microparticles is measured by means of the microparticle measuring instrument indicated in FIG. 1.

At first, the label microparticles bound to the well are suspended in a solution. For example, a HCl-glycine buffer solution of pH2 is added in the well to cut the binding of the label microparticles. In this way they are again suspended in the solution to obtain suspension of the microparticles. The binding of the label microparticles may be cut also by a mechanical method by making ultrasonic wave, etc., act thereon.

Then the number of the label microparticles in this label microparticle suspension is counted by means of the measuring instrument indicated in FIG. 1. Based on the count value thus obtained, it is possible to measure quantitatively the amount of AFP, which is the material to be measured.

Figure 7:
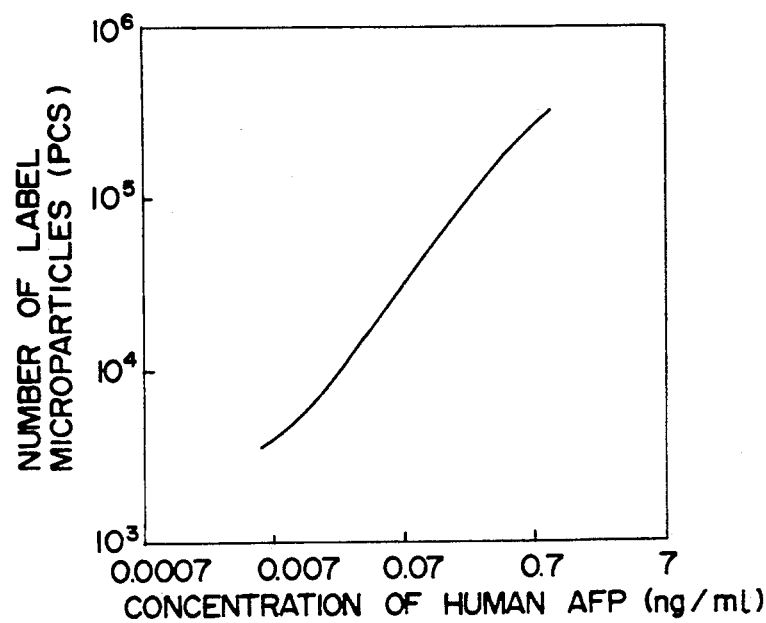
FIG. 7 is a graph representing the relation between the concentration of human AFP in a sample solution and the number of counted label microparticles.

This is made possible by measuring previously the number of label microparticles for predetermined concentrations of the material to be measured to trace a calibration curve for this purpose. When a certain amount of the label microparticle suspension, in which label microparticles are again suspended, is measured to obtain the relation between the concentration of the human AFP in the sample solution and the counted number of the label microparticles, a curve indicated in FIG. 7 is obtained. In this way it is possible to measure quantitatively human AFP of extremely low concentration. Since the number of molecules of the material to be measured corresponds in principle to the total number of the fluorescent microparticles, a precise quantitative measurement is possible.

In the present embodiment, since fluorescent microparticles can be counted with a high precision, the amount of the material to be measured can be measured quantitatively with a high precision. Although, in the present embodiment, only a certain amount of the microparticle suspension has been measured, it is possible also to measure the whole amount of the microparticle suspension. In the case where the whole amount is measured, the total number of the microparticles can be counted and thus the amount of the material to be measured can be measured quantitatively with a high precision. This is possible also if only a part of the microparticle suspension is measured as in the present embodiment. In this case it is possible to count them with a high reproducibility by controlling various conditions such as the amount of the measured solution, the point of time of starting the measurement, etc., so as to be constant.

Further, there are roughly two methods for stripping off the fluorescent microparticles caught by the reaction tube. That is, they are a case where all the fluorescent microparticles are stripped off and a case where an antigen-antibody reaction part is stripped off specifically. In the former case, the fluorescent microparticles bound with the reaction tube by non-specific adsorption such as physical adsorption are also stripped off, but the operation is relatively simple. In the latter case, it is possible to strip off selectively only the fluorescent microparticles by the antigen-antibody reaction with the material to be measured, and thus the sensitivity of the quantitative measurement can be further increased.

Further, although, in the present embodiment, fluorescent microparticles bound to the reaction tube are stripped off after the reaction to obtain again a microparticle suspension solution, which microparticles are counted by means of the instrument using the flow method indicated in FIG. 1, the method for counting fluorescent microparticles can be carried out also by means of the instrument indicated in FIG. 5. That is, it is possible also to count the fluorescent microparticles in the tube by holding the reaction tube, with which the fluorescent microparticles are bound, on the X-Y scanning stage, which is moved in the X-Y directions.

Further, although, in the present embodiment, an example, in which human AFP is measured quantitatively as the material to be measured, is shown, it is possible also to measure quantitatively other antigens, hormones, etc., by an identical immunological measurement.

Furthermore, this method is useful also for detecting DNA having a specific base sequence. Concretely speaking, a probe DNA-microparticle complex, in which a probe DNA recognizing the base sequence to be detected is bound with a fluorescent microparticle, is prepared. At first, the DNA in the sample is made in a state of one chain by thermal denature, alkali denature, etc., which is bound with a solid phase such as a film, etc. The probe DNA-microparticle complex is made to react therewith to cause a hybridization reaction. After having been rinsed, the probe DNA-microparticle complex is stripped off by producing denature, etc., to obtain a microparticle suspension. This microparticle suspension is analyzed by means of the instrument indicated in FIG. 1 and the number of microparticles is counted. The number of probe DNAs can be detected, starting from this count value and thus the amount of the target DNA in the sample can be measured. By this method, since probe DNA molecules can be detected in an imitating manner through microparticles, the quantitative measuring method can be realized with a high sensitivity.

Figure 8:
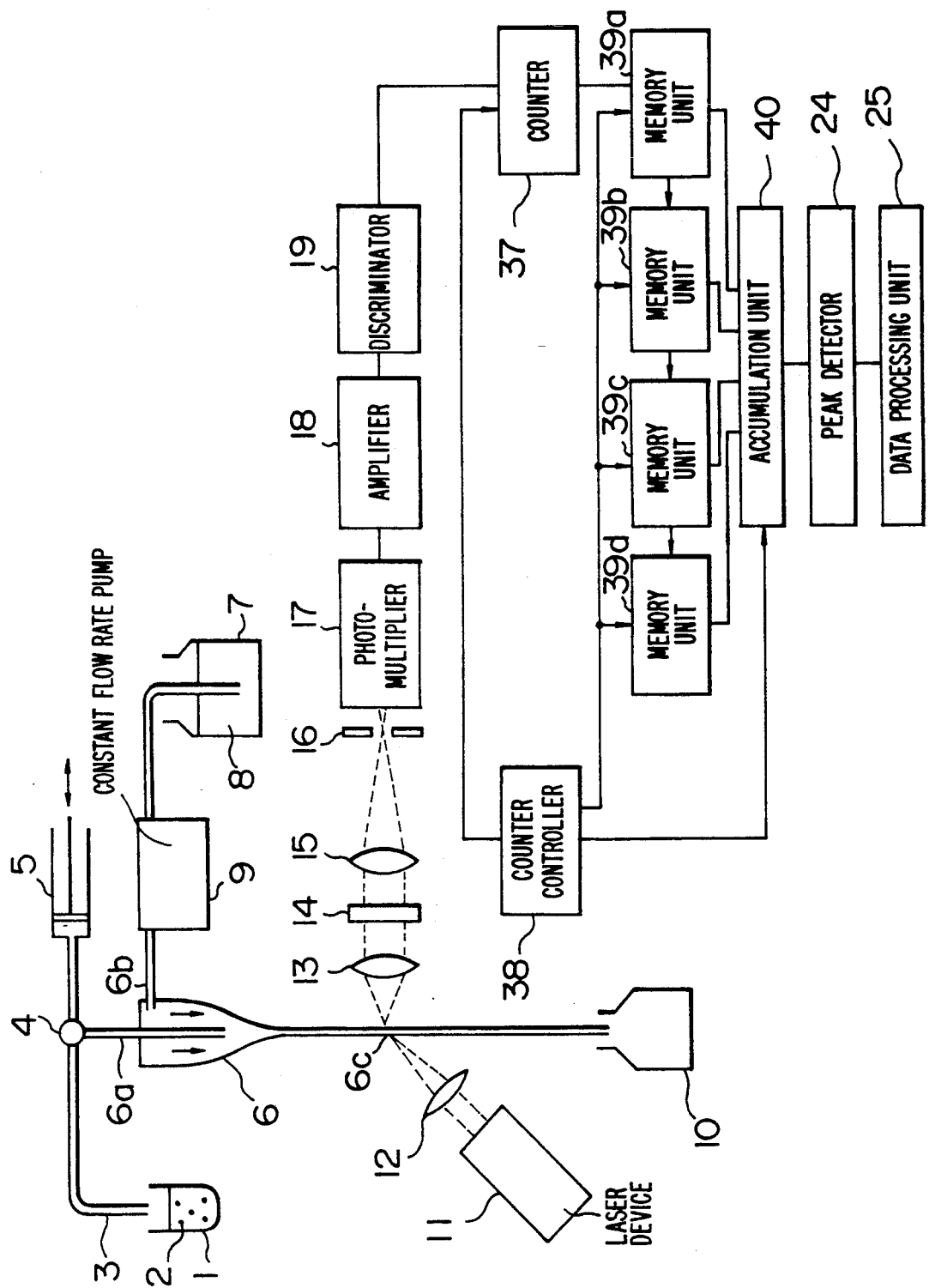
FIG. 8 is a block diagram of an instrument for measuring fluorescent microparticles indicating a sixth embodiment of the present invention.

FIG. 8 is a block diagram of a microparticle measuring instrument, which is a sixth embodiment of the present invention.

In FIG. 8, what is different from the construction indicated in FIG. 1 is the part after the discriminator 19. That is the counter unit is composed of one counter 37 and the counter control unit is composed of a counter controller 38. The accumulating circuit unit consists of memory units 39a to 39d and an accumulation unit 40. The peak detecting unit consists of a peak detector 24 and the data processing unit consists of a data processor 25 such as a pulse height analyzer, a counter, a computer, etc.

The sample solution to be measured and a sheath solution are led to a sheath flow cell so that the sample solution is a fine stream enclosed by the sheath solution and fluorescence is measured. For this purpose, at first, the microparticle suspension 2 in the tube 1 is sucked by means of a syringe pipetter 5 through the nozzle 3 and the electromagnetic valve 4. Then the electromagnetic valve 4 is switched over so that the sucked microparticle suspension 2 is ejected with a constant flow rate from the sample introducing tube 6a in the sheath flow cell 6. The microparticle suspension solution 2 is narrowed finely and made to pass through the light measuring portion 6c in the sheath flow cell 6 by introducing at the same time the sheath solution 8 in the bottle of the sheath solution 7 through the sheath solution introducing tube 6b in the sheath flow cell 6 by means of a constant flow rate pump 9. Finally, it is discarded in a waste bottle 10.

In order to excite fluorescent microparticles, laser light emitted by the laser device 11 is collected by the lens 12 so that the microparticle suspension solution 2 flowing through the light measuring portion 6c in the sheath flow cell 6 is irradiated therewith. Fluorescence emitted by the fluorescent microparticles is collected by the lens 13. Scattered light is removed as far as possible by the spectral filter 14 such as a bandpass interference filter, etc. Transmitted fluorescence is collected again by the lens 15 so as to be focused on the slit 16. In this way only an image from the fluorescent microparticles is made to pass through and is detected by the photomultiplier 17 acting as the photodetector. The output of the photomultiplier 17 is amplified by the amplifier 18, based on the photoelectron counting method. Thereafter it is sent to the discriminator 19. In this way photons injected into the photomultiplier 17 are converted into a pulse signal, which is outputted.

Next pulse signals thus obtained, based on the detection of photons, are counted by the counter 37. The operation of the counter 37 is controlled by the counter controller 38. The counter controller 38 controls a predetermined timing and the repetition period (T). The repetition period (T) is shorter than the period of time, during which the fluorescent microparticles pass through the excitation light beam to emit fluorescence. Here explanation is made, supposing that the period (T) is ¼ of the period of time, during which the fluorescence is emitted. The output and reset operation of the count result of the counter 37 is set so as to be effected instantaneously and the gate time is set so as to be approximately equal to the period (T).

The count value of the counter 37 for every period is outputted to the memory 39a and stored therein. At the same time the immediately preceding values stored in the memories 39a, 39b and 39c are transferred to the memories 39b, 39c and 39d, respectively. This operation is effected by using a trigger synchronized with the repetition period (T) from the counter controller 38 so that the memories are operated in synchronism with the output of the count value for every period (T) of the counter 37. The count value is transferred in the order of the memories 39a→39b→39c→39d so that at an arbitrary point of time the newest count value is stored in the memory 39a, the count value preceding by one period in the memory 39b, the count value preceding by two periods in the memory 39c, and the count value preceding by three periods in the memory 39d. That is, the count values for 4 periods are stored and the total count value in a time region, which is substantially $4 \times T$ long, is obtained by accumulating these values by means of the accumulation unit 40. This operation is effected for every period (T) and as the result the total number of photons detected in the time region of $4 \times T$ is obtained for every period of time of T successively in real time.

The peak detector 24 obtains a peak of the count value from variations in time in this count value, which is analyzed by the data processing unit 25. The data processing unit 25 accumulates the frequency of the peak value and effects a processing of calculating the total number of pulses, i.e. the number of microparticles, having the peak value in a specified region.

Figure 9:
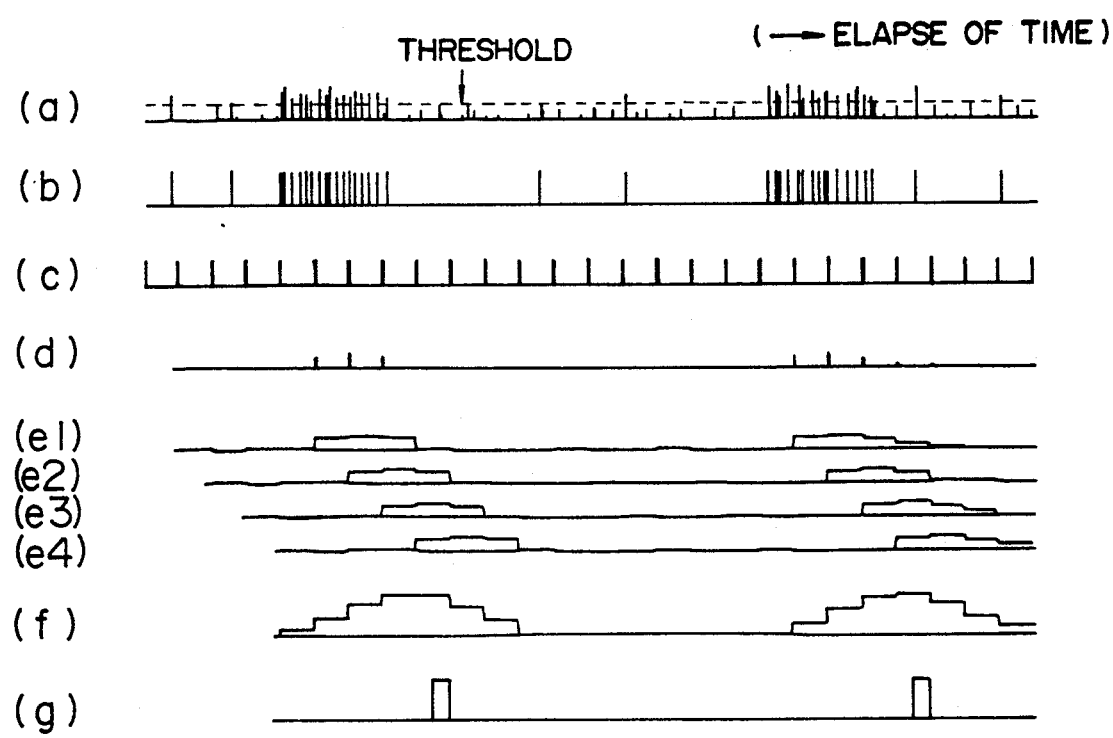
FIG. 9 is a time chart representing a flow of signal processing in the instrument indicated in FIG. 8.

FIG. 9 is a time chart showing a flow of the signal processing for the instrument indicated in FIG. 8.

(a) indicates variations in time in the output of the photomultiplier 17. This output includes pulses relatively great, based on the detection of photons, and pulses relatively small due to dark current in the photomultiplier 17. These two sorts of pulses are discriminated by the amplifier 18 and the discriminator 19, using a threshold as the boundary therebetween, and only the pulses, based on the detection of photons are taken out, as indicated in (b). (c) indicates variations in time in the gate signal for the counter outputted by the counter controller 38. The indication means that the counting operation of the counter is started at the low level. (d) indicates variations in time in the output of the count value of the counter 37 obtained as the result. Although, in the indication, the gate signals are indicated with an enlarged interval, in order to facilitate the explanation, in reality the time interval is negligibly small with respect to the width in time of the gate signals. (e1) to (e4) indicate variations in time in the count values stored in the memories 39a to 39d, respectively. The count value of the counter 37 is stored at first in the memory 39a and has variations in time indicated in (e1). (e2) to (e4) show variations in time obtained by delaying (e1) by one, two and three periods, respectively. (f) indicates a result obtained by accumulating (e1) to (e4) by means of the accumulation unit 40. (g) indicates the peak value obtained by the peak detector 24, starting from the signal indicated in (f). This peak value and the frequency thereof are analyzed in the data processing unit 25. The total number of microparticles can be calculated from the production frequencies of pulses having peak values in specified regions.

Figure 11:
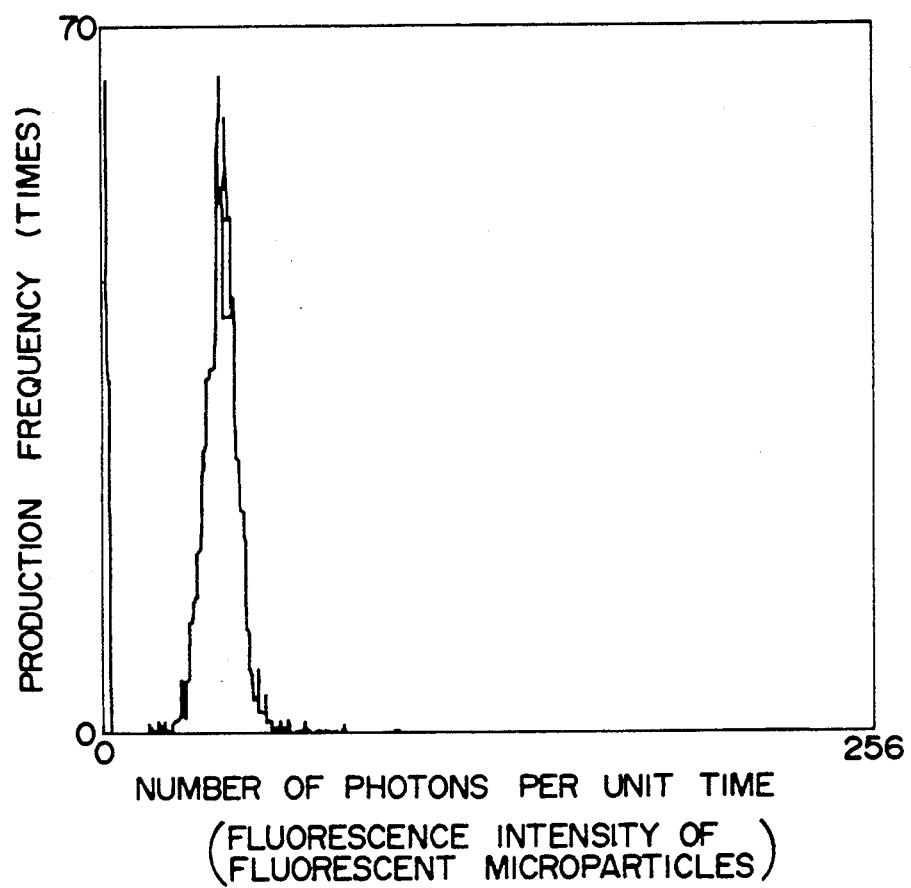
FIG. 11 is a histogram indicating the relation between the umber of photons detected for every standard period obtained by means of the instrument indicated in FIG. 8 and the production frequency thereof.

Concretely speaking, an argon ion laser (wavelength of 488 nm, output of 15 mW) is used and light emitted thereby is suitably attenuated by means of a neutral density filter. The light measuring portion in the sheath flow cell is irradiated with a laser light beam narrowered so as to have a diameter of about 20 $\mu$m. Polystyrene microparticles (diameter of 0.09 $\mu$m) containing fluorescein are used for the fluorescent microparticles. The microparticle suspension 2 is led to the sheath flow cell. The fluorescent microparticle suspension 2 is narrowed to a fine stream having a diameter of about 10 $\mu$m, which is made to pass through the light measuring portion. The flow speed is adjusted to about 0.3 m/s. Fluorescence thus produced is collected by an objective lens having a magnification factor of 40, transformed into a parallel light beam, and spectroscopically decomposed by an interference filter transmitting light of 510 to 550 nm. Next, an image of flowing fluorescent microparticles is focused on a slit having a rectangular aperture having a width of 500 $\mu$m and a length of 1 mm. Transmitted fluorescence is detected by the photomultiplier and subjected to the signal processing described previously. The repetition period of the counter is 20 $\mu$s, which is about ¼ of the period of time, during which the microparticles are irradiated with laser light. The result obtained at that time shows characteristics as indicated in FIG. 11. The abscissa in FIG. 11 represents the peak value obtained by the peak detector, which means the number of photons of fluorescence for every substantial count time (80 $\mu$s), i.e. every fluorescence emitting time, accumulated by the accumulation unit, proportional to the fluorescence intensity. On the other hand the ordinate represents the production frequency of that value. The protrusion at the part corresponding to small numbers of photons on the abscissa represents a part of a tail of the protrusion due to noise. The protrusion at the part corresponding to great numbers of photons represents signals coming from the fluorescent microparticles. The integral value of this protrusion is calculated as the total number of the detected fluorescent microparticles.

Although, in FIG. 8, a case where 4 memories are used is indicated, a similar system can be realized by using n memories, n being greater than 2, and by setting the gate time of the counter at about 1/n of the period of time, during which fluorescence is emitted. In order to increase the precision, it is preferable to increase further the magnitude of n. By the construction described in the present embodiment it is possible to obtain an effect identical to that obtained in the first embodiment.

Figure 10:
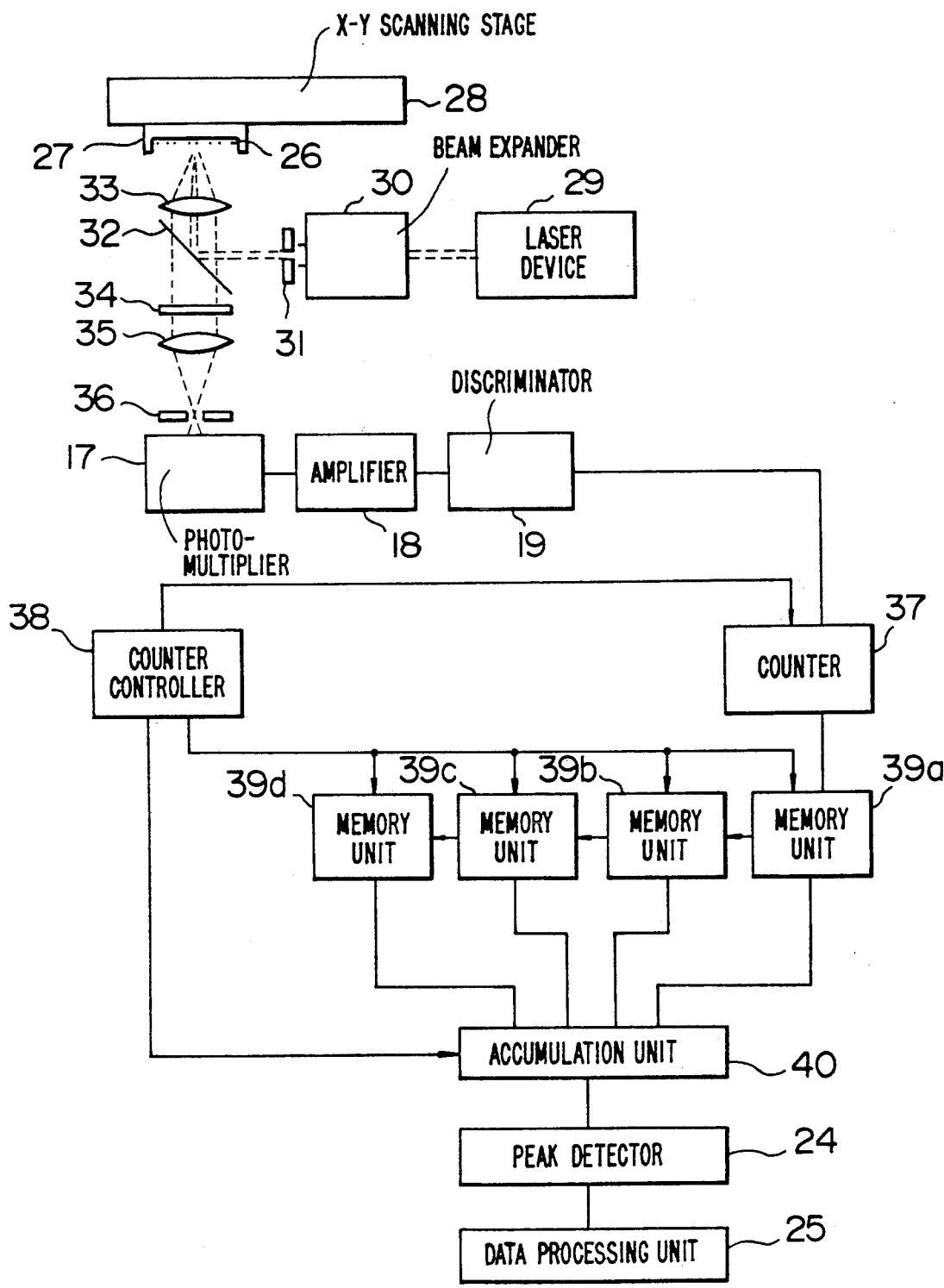
FIG. 10 is a block diagram of an instrument for measuring fluorescent microparticles indicating a seventh embodiment of the present invention.

FIG. 10 is a block diagram of a microparticle measuring instrument, which is a seventh embodiment of the present invention. Here an instrument for measuring fluorescent microparticles stuck on a substrate is indicated.

What is different in FIG. 10 from the construction indicated in FIG. 5, is the part, after the discriminator 19. The part after the discriminator 19 is identical to the corresponding part of the construction indicated in FIG. 8.

An argon ion laser (wavelength of 488 nm, output of 15 mW) is used for the laser device 29. Light emitted thereby is attenuated by a neutral density filter, etc. Fluorescent microparticles are irradiated with a spot of a square of 1 $\mu$m. The sample is moved successively in the X-Y directions with a speed of 5 mm/s by means of the X-Y scanning stage 28. The working time of the counter at this time is 60 $\mu$s. The result obtained at this time is a histogram having a distribution almost identical to that indicated in FIG. 11.

We claim:

1. A microparticle measuring method for counting fluorescent microparticles to be analyzed, comprising the steps of:

leading fluorescent microparticles contained in a liquid to a narrow flow path and introducing said fluorescent microparticles substantially one after another into a position irradiated with excitation light in said narrow flow path said position being irradiated with excitation light for generating fluorescence from said fluorescent microparticles; or leading an excitation light beam for generating fluorescence and having a width sufficiently narrow for where substantially one fluorescent microparticle among fluorescent microparticles bound to a solid phase can exist, to a position of said fluorescent microparticle while sweeping the beam successively;

irradiating said fluorescent microparticles contained in the liquid or said fluorescent microparticles bound to the solid phase with the excitation light;

taking out signal pulses produced by detection of a single photon of fluorescence generated by the irradiation with said excitation light;

counting the signal pulses with N (N≧2) counters, a counting working time of each counter being equal to a predetermined standard period, a counting repetition period (T) of each counter being longer than said counting working time, phases of the counters being shifted by 1/N from each other, and a working interval between the n-th (N≧n≧2) and (n−1)-th counters being equal to T/N;

successively taking out count values of the counters at intervals of T/N;

obtaining a count value representing a number of the signal pulses per said predetermined standard period based on the successively taken out count values; and recognizing existence of said fluorescent microparticle based on the count value representing a number of signal pulses per said predetermined standard period.

2. A microparticle measuring method according to claim 1, wherein the step of recognizing the existence of said fluorescent microparticle includes recognizing the existence of said fluorescent microparticle when said count value representing a number of signal pulses per said predetermined standard period exceeds a predetermined threshold.

3. A microparticle measuring method according to claim 1, wherein said predetermined standard period is approximately equal to a period of time during which said fluorescent microparticle is irradiated with light, or is shorter than a period of time which is approximately twice as long as the period of time during which said fluorescent microparticle is irradiated with light.

4. A microparticle measuring method according to claim 1, wherein said fluorescent microparticles having a diameter smaller than 0.1 μm.

5. An assay method for measuring a material, the assay method employing a microparticle measuring method according to claim 1 and comprising the steps of:

binding fluorescent microparticles to a solid phase; and measuring the fluorescent microparticles bound to the solid phase with the microparticle measuring method according to claim 1;

wherein the step of binding fluorescent microparticles to a solid phase includes obtaining a solid phase obtained by immobilizing a material which is bound specifically with the material to be measured in a sample to be measured, or a solid phase to which the material to be measured can be bound, obtaining fluorescent microparticles obtained by immobilizing a material which is bound specifically with the material to be measured, and bringing said solid phase, the material to be measured, and said fluorescent microparticles in contact with each other.

6. An assay method for measuring a material, the assay method employing a microparticle measuring method according to claim 5 and comprising the steps of:

binding fluorescent microparticles to a solid phase;

stripping out the fluorescent microparticles bound to the solid phase to form a suspension of the fluorescent particles in a liquid; and measuring the fluorescent microparticles in the liquid with the microparticle measuring method according to claim 5;

wherein the step of binding fluorescent microparticles to a solid phase includes obtaining a solid phase obtained by immobilizing a material which is bound specifically with the material to be measured in a sample to be measured, or a solid phase to which the material to be measured can be bound, obtaining fluorescent microparticles obtained by immobilizing a material which is bound specifically with the material to be measured, and bringing said solid phase, the material to be measured, and said fluorescent microparticles in contact with each other.

7. A microparticle measuring method for counting fluorescent microparticles to be analyzed, comprising the steps of:

leading fluorescent microparticles contained in a liquid to a narrow flow path and introducing said fluorescent microparticles substantially one after another into a position irradiated with excitation light in said narrow flow path said position being irradiated with excitation light for generating fluorescence from said fluorescent microparticles; or leading an excitation light beam for generating fluorescence and having a width sufficiently narrow for irradiating a region where substantially one fluorescent microparticle among fluorescent microparticles bound to a solid phase can exist, to a position of said fluorescent microparticle while sweeping the beam successively;

irradiating said fluorescent microparticles contained in the liquid or said fluorescent microparticles bound to the solid phase with the excitation light;

taking out signal pulses produced by detection of a single photon of fluorescence generated by the irradiation with said excitation light;

counting the signal pulses with N (N≧2) counters, a counting working time of each counter being equal to a predetermined standard period, a counting repetition period (T) of each counter being longer than said counting working time, phases of the counters being shifted by 1/N from each other, and a working interval between the n-th (N≧n≧2) and (n−1)-th counters being equal to T/N successively taking out count values of the counters at intervals of T/N;

obtaining a count value representing a number of the signal pulses per predetermined standard period based on the successively taken out count values; and recognizing existence of said fluorescent microparticle when said count value representing a number of the signal pulses per predetermined standard period exceeds a predetermined threshold;

wherein said predetermined standard period is approximately equal to a period of time during which said fluorescent microparticle is irradiated with light, or is shorter than a period of time which is approximately twice as long as the period of time during which fluorescent microparticle is irradiated with light.

8. A microparticle measuring method according to claim 7, wherein said fluorescent microparticles having a diameter smaller than 0.1 μm.

* * * * *